(12) United States Patent
Yamagami et al.

(10) Patent No.: US 6,392,083 B2
(45) Date of Patent: May 21, 2002

(54) PROCESS FOR PRODUCING SALTS OF CYANOBENZYLAMINES

(75) Inventors: Isao Yamagami, Fukushima; Hiroshi Yasuda, Chiba; Masatoshi Murakami, Kawasaki; Toru Yoshida, Fukushima, all of (JP)

(73) Assignee: Showa Denko K.K., Tokyo (JP)

( * ) Notice: Subject to any disclaimer, the term of this patent is extended or adjusted under 35 U.S.C. 154(b) by 0 days.

(21) Appl. No.: 09/875,094

(22) Filed: Jun. 7, 2001

Related U.S. Application Data

(63) Continuation of application No. PCT/JP00/08874, filed on Dec. 14, 2000.
(60) Provisional application No. 60/246,588, filed on Nov. 8, 2000.

(30) Foreign Application Priority Data

Dec. 14, 1999 (JP) ............................................. 11-353862

(51) Int. Cl.[7] ............................................... C07C 51/41
(52) U.S. Cl. ........................................................ 558/422
(58) Field of Search ........................................... 558/422

(56) References Cited

U.S. PATENT DOCUMENTS 3,515,741 A * 6/1970 Thoma et al. ............... 260/465
3,644,469 A * 2/1972 Koppe et al. ................ 260/465
4,101,671 A * 7/1978 Keck et al. .................. 424/330

FOREIGN PATENT DOCUMENTS

| EP | 0 776 883 A1 | 6/1997 | ......... C07C/213/10 |
| GB | 814631 | 6/1959 | |
| WO | 95/29189 | 11/1995 | ............ C07K/5/08 |
| WO | 99/64391 | 12/1999 | ......... C07C/255/58 |

OTHER PUBLICATIONS

International Search Report.
Chemical Abstracts, vol. 58, 1963, Column 5468d.

* cited by examiner

*Primary Examiner*—Floyd D. Higel
*Assistant Examiner*—Golam M. M. Shameem
(74) *Attorney, Agent, or Firm*—Sughrue Mion, PLLC

(57) ABSTRACT

A process for producing a salt of a cyanobenzylamine comprising reacting a cyanobenzylamine with an acid. A salt of a cyanobenzylamine can industrially easily be produced and the resulting salt of a cyanobenzylamine has a high bulk density.

13 Claims, No Drawings

PROCESS FOR PRODUCING SALTS OF CYANOBENZYLAMINES

CROSS-REFERENCE TO RELATED APPLICATIONS

This application is based upon and claims priority of Japanese Patent Application No. 11-353862, filed Dec. 14, 1999, and is a continuation of PCT/JP00/08874 filed Dec. 14, 2000.

This application is an application filed under 35 U.S.C. § 111(a) claiming benefit pursuant to 35 U.S.C. § 119(e)(1) of the filing date of the Provisional Application 60/246,588 filed Nov. 8, 2000, pursuant to 35 § 111(b).

BACKGROUND OF THE INVENTION

1. Field of the Invention

The present invention relates to a process for producing salts of cyanobenzylamines, and to the salts of cyanobenzylamines obtained by the process. The salts of cyanobenzylamines obtained according to the present invention serve as useful intermediates in the production of pharmaceuticals and agrochemicals.

2. Description of the Related Art

Conventionally, there have been known, for example, processes for producing salts of cyanobenzylamines, employing p-cyanobenzyl bromide as a starting material, as described below.

J. Org. Chem., 63 (1998) 19, 6715–6718 discloses a relevant process including reacting p-cyanobenzyl bromide with hexamethylenetetramine and, subsequently, reacting the reaction mixture with hydrogen chloride dissolved in ethanol.

J. Am. Chem. Soc., 81 (1959), 4328, discloses a process for synthesizing 4-aminobutyronitrile hydrochloride including reacting hydrazine with N-(3-cyanopropyl)phthalimide synthesized from 4-bromobutyronitrile; post-treating the resultant reaction product; and reacting the post-treated product in diethyl ether with anhydrous hydrogen chloride. The reference discloses that p-cyanobenzylamine hydrochloride is synthesized through a method similar to this method.

J. Med. Chem., 10 (1967), 833–840, discloses a process for producing p-cyanobenzylamine from α-phthalimido-p-tolunitrile and hydrazine. The reference discloses synthesis of p-cyanobenzylamine hydrochloride, but does not disclose details of the method used for the synthesis.

Japanese International Application Domestic Publication No. 10-503477 discloses a process for synthesizing p-cyanobenzylamine hydrochloride including reacting hydrazine with N-(4-cyanophenyl)methylphthalimide prepared from p-cyanobenzyl bromide and potassium phthalimide; post-treating the resultant reaction product; and transforming the treated product into hydrochloride. However, the step of transforming the treated product into hydrochloride is not described in detail.

Japanese International Application Domestic Publication No. 9-509937 discloses a process for synthesizing p-cyanobenzylamine hydrochloride including reacting N-Boc-p-aminomethylbenzonitrile with hydrogen chloride gas in ethyl acetate.

In addition, identification of p-cyanobenzylamine as a hydrochloride thereof is reported in Chem. Ber., 34 (1901), 3368, but the identification method is not described.

Thus, these processes for producing salts of cyanobenzylamines are unsatisfactory as industrial production processes, since the processes require a number of reaction steps and attain an insufficient level of production yield.

In addition, the aforementioned references fail to disclose characteristic drawbacks arising during industrial production of cyanobenzylamine hydrochlorides. Specifically, problems in terms of product distribution, such as space required for storage and ease of transportation, and those in terms of production apparatus, such as vessels having the required capacity, are not identified, and the means for solving these problems have not been elucidated.

As far as the present inventors know, cyanobenzylamine hydrochlorides are bulky compounds, having bulk densities of 0.2 g/ml or less. The high bulkiness results in the necessity of providing an extensive area for storage in the case of industrial production and use of cyanobenzylamine hydrochlorides. Generally, suitable transportation means is chosen based on the weight of matter. However, when such bulky matter is handled, the forms of transportation means are limited because of the volume thereof. This is very disadvantageous in view of distribution costs. In addition, when a cyanobenzylamine hydrochloride is handled in a production apparatus, scaling-up the apparatus is needed, due to the low bulk density of the compound, increasing apparatus costs as well as causing inconvenience during operation.

BRIEF SUMMARY OF THE INVENTION

Thus, it is an object of the present invention to provide an industrially suitable process for producing a salt of a cyanobenzylamine at high yield and in a simple manner. It is another object to provide a less-bulky salt of a cyanobenzylamine having a lower bulk density.

The present inventors have conducted extensive studies in order to solve the aforementioned problems, and have found that a salt of a cyanobenzylamine can be produced in a simple manner by reacting a cyanobenzylamine with an acid, and that, when the acid is used in the form of an aqueous solution, the produced cyanobenzylamine salt is endowed with a remarkably high bulk density as compared with a similar compound produced through a conventional process. On the basis of these findings, the inventors have further found that, by applying a salt of a cyanobenzylamine to the industrial production of chemicals, the distribution, including storage and transportation, as well as operability in relation to a production apparatus, can be remarkably improved. The present invention has been accomplished on the basis of the above findings.

Accordingly, the present invention provides a process for producing a salt of a cyanobenzylamine comprising reacting a cyanobenzylamine with an acid.

The invention also provides a salt of a cyanobenzylamine having a bulk density of 0.4 g/ml or more.

DETAILED DESCRIPTION OF THE INVENTION

Upon the practice of the process of the invention, in general, a cyanobenzylamine may advantageously be reacted with an acid, optionally in a solvent, for a predetermined period of time while stirring, to thereby form a suspension of a salt of a cyanobenzylamine.

The cyanobenzylamines usable for the invention may preferably be compounds represented by the following formula.

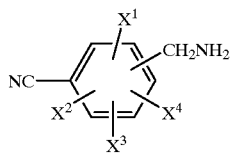

wherein $X^1$, $X^2$, $X^3$ and $X^4$ each independently represent a hydrogen atom, an alkyl group having 1 to 3 carbon atoms or a halogen atom, and the —$CH_2NH_2$ group may be at any position of ortho, metha or para to the —CN group.

Specific examples of the compounds may include unsubstituted cyanobenzylamines such as o-cyanobenzylamine, m-cyanobenzylamine and p-cyanobenzylamine, and substituted cyanobenzylamines such as 2-alkyl-4-cyanobenzylamine, 2-chloro-4-cyanobenzylamine, tetrafluorocyanobenzylamine and tetrachlorocyanobenzylamine.

Cyanobenzylamines can be produced through any of the known processes. For example, m-cyanobenzylamine and p-cyanobenzylamine can be readily synthesized through the process disclosed in Japanese Unexamined Patent Publication (kokai) No. 9-40630 by subjecting one nitrile group of isophthalonitrile and that of terephthalonitrile to reduction, respectively.

In the invention, cyanobenzylamine hydrates can also be employed as the starting material. Examples of the hydrates may include o-, m-, and p-cyanobenzylamine hydrates, with p-cyanobenzylamine hydrate being preferred.

Cyanobenzylamine hydrates can be produced through any of the known processes. For example, m-cyanobenzylamine hydrate and p-cyanobenzylamine hydrate can be readily synthesized through the process disclosed in Japanese Examined Patent Publication (kokoku) No. 40-10133, from m-cyanobenzylamine and p-cyanobenzylamine, respectively.

No solvent may be required in the reaction employed in the process of the invention. However, a solvent may be used so as to dilute the salt of a cyanobenzylamine to facilitate handling of the salt in the form of a suspension. Examples of preferred organic solvents may include toluene, ethyl acetate, and methylene chloride, which do not react with cyanobenzylamines or salts thereof and do not cause side reactions when the reaction system contains an acid. Such an organic solvent is used in an amount such that a salt of a cyanobenzylamine can be handled in the form of a suspension. Typically, the solvent may be used in an amount 0.1–10 times the mass of the employed cyanobenzylamine.

A preferred solvent to be employed in the process of the invention may be water. When water is used as a solvent, a salt, especially hydrochloride, of cyanobenzylamine having a bulk density of 0.4 g/ml or more can be obtained. Such a high-bulk-density cyanobenzylamine salt advantageously reduces distribution costs, particularly for industrial use.

Water serving as a solvent may be used in an amount such that the cyanobenzylamine salt can be handled in the form of a suspension. Preferably, water is used in an amount 0.1–10 times the mass of the employed cyanobenzylamine. When the amount is less than 0.1 times the mass, the formed suspension of the cyanobenzylamine salt may become more viscous, thereby causing problems such as difficulty in stirring during reaction, whereas when the amount is 10 times or more the mass, the formed cyanobenzylamine salt may dissolve in water, disadvantageously decreasing the yield.

When water is employed as a solvent in the process of the present invention, impurities contained in the cyanobenzylamine, that are difficult to remove through such purification methods as distillation, can be readily removed. Specifically, the impurities can be removed by utilizing the difference in solubility in water between the cyanobenzylamine salt and the impurity salts. Thus, a high-purity cyanobenzylamine salt can be obtained.

More specifically, when p-cyanobenzylamine is synthesized by reducing one nitrile group of terephthalonitrile (see, Japanese Unexamined Patent Publication (kokai) No. 9-40630) for example, p-xylylenediamine is by-produced in addition to the formed p-cyanobenzylamine. p-Xylylenediamine has a boiling point of 127.6° C./590 Pa, and p-cyanobenzylamine has a boiling point of 132.4° C./550 Pa. These two compounds are difficult to separate through distillation due to the small difference between their respective boiling points. In accordance with the present invention, when p-cyanobenzylamine containing p-xylylenediamine as an impurity is reacted with hydrogen chloride in water, high purity p-cyanobenzylamine hydrochloride can be obtained in the form of a solid, since the water solubility of p-cyanobenzylamine hydrochloride is much lower than that of p-xylylenediamine hydrochloride.

Where a cyanobenzylamine employed contains substances having a boiling point much higher than that of the cyanobenzylamine, such as tar-like substances, through the decomposition of the cyanobenzylamine, it is preferable that the high boiling point substances are preliminarily removed by distillation or the like before carrying out the process of the invention, since thereby a cyanobenzylamine salt of high crystallinity and high purity is obtained.

The acid to be employed in the invention is not particularly limited as far as it produces a salt of a cyanobenzylamine according to the process of the invention. Specific examples thereof may include hydrogen chloride, sulfuric acid, acetic acid, trifluoroacetic acid and propionic acid.

Where hydrogen chloride is employed as the acid, it may be in the form of gas or an aqueous solution. When hydrogen chloride gas is used, the gas itself, optionally diluted with an inert gas, is blown into a solution of the cyanobenzylamine, or alternatively, passed through a vapor phase cyanobenzylamine. The ratio of hydrogen chloride to an inert gas is not particularly limited.

When an aqueous solution of hydrogen chloride is used, the solution may be added dropwise to the cyanobenzylamine (or a solution thereof) or the cyanobenzylamine (or a solution thereof) may be added dropwise to the hydrogen chloride solution. No particular limitation is imposed on the concentration of hydrogen chloride in the solution, and an aqueous solution of hydrogen chloride industrially readily available may be used. Preferably, the concentration is 1–37 mass %, more preferably 5–37 mass %. When the concentration is low, the amount of filtrate during separation of the cyanobenzylamine hydrochloride from water through filtration increases, thereby increasing loss of the product due to dissolution and decreasing the product yield. In addition, it is difficult to achieve a concentration of 37 mass % or more with an industrially produced aqueous solution of hydrogen chloride.

Where the acid employed is a monobasic one such as hydrogen chloride, since the acid reacts with an amino group of the cyanobenzylamine in equimolar amounts, the amount of the acid may theoretically be equimolar to the cyanobenzylamine. However, the acid chloride is preferably used in an amount of 0.9–2.0 moles per 1 mole of the cyanobenzylamine in practice, since the cyanobenzylamine usually contains a certain amount of impurity.

Where the acid employed is a dibasic one such as sulfuric acid, a primary sulfate of the cyanobenzylamine is formed through the reaction of 2 moles of the cyanobenzylamine and 1 mole of sulfuric acid when sulfuric acid is used in an amount of 2/1 mole per 1 mole of the amino group in the cyanobenzylamine, and a secondary sulfate is formed through the reaction of the cyanobenzylamine and sulfuric acid in equimolar amounts when sulfuric acid is used in an amount of equimolar to the cyanobenzylamine.

The temperature of the reaction between a cyanobenzylamine and an acid is not particularly limited so long as the temperature is not lower than the melting point and not higher than the boiling point of the employed solvent. The reaction temperature is preferably 0–100° C. in view of the operability and the like.

The cyanobenzylamine salt powder thus formed is separated from the suspension and dried, through a known method.

The present invention will be further illustrated below by way of examples, which should not be construed as limiting the invention thereto.

In the following examples, cyanobenzylamines and xylylenediamines were quantitated by means of high-performance liquid chromatography under the following conditions.

High-performance Liquid Chromatographic Analysis Conditions

Column: Shodex NN-614 (product of SHOWA DENKO K.K.)

Eluent: Mixture containing monosodium phosphate anhydrate (7.2 g), water (700 ml), and acetonitrile (300 ml)

Detector: UV detector

Hydrogen chloride was quantitated through anion chromatography under the following conditions.

Anion Chromatographic Analysis Conditions

Column: IonPac AS12A 4 mm (product of DIONEX)

Eluent: Aqueous solution containing sodium carbonate (2.7 mmol/l)+Sodium hydrogencarbonate (0.3 mmol/l)

The bulk density was measured with a Powder-tester Type PT-N (product of Hosokawa Micron).

PREPARATION EXAMPLE 1

Synthesis of Crude p-cyanobenzylamine

Crude p-cyanobenzylamine was synthesized in accordance with the process described in Japanese Unexamined Patent Publication (kokai) No. 9-40630 as follows.

Into a 100 ml autoclave, methanol (30 ml) and sponge nickel (R-2400, product of W.R. Grace & Co.) (1.0 g) were placed, and the internal pressure of the autoclave was elevated to 1.0 MPa by introducing hydrogen. The mixture contained in the autoclave was stirred while heating at 150° C. for one hour. Terephthalonitrile (5.0 g) and sodium hydroxide (0.1 g) were introduced into the reactor, and the internal pressure was elevated to 0.5 MPa at ambient temperature while introducing hydrogen. Under monitoring of the hydrogen absorbing rate, when the hydrogen pressure was dropped to 0.1 MPa, the pressure was elevated again to 0.5 MPa. This pressure control operation was repeated. Reaction was terminated when the hydrogen absorption ratio reached 115% of the theoretical value.

From the thus-obtained reaction mixture, methanol was removed through distillation. The resultant mixture was subjected to a further distillation at a high temperature under a reduced pressure, thereby removing crude p-cyanobenzylamine. Through high-performance liquid chromatographic analysis of the distillate, the p-cyanobenzylamine content and the p-xylylenediamine content were found to be 93 mass % and 7 mass %, respectively.

PREPARATION EXAMPLE 2

Synthesis of p-Cyanobenzylamine Hydrate p-Cyanobenzylamine hydrate was synthesized in accordance with the method described in Japanese Examined Patent Publication (kokoku) No. 40-10133 as follows.

Crude p-cyanobenzylamine (32 g) obtained in Preparation Example 1 was added dropwise to water (100 g) at room temperature, thereby forming a slurry containing p-cyanobenzylamine hydrate. The slurry was subjected to filtration, and the thus-separated solid was washed with water, to thereby yield p-cyanobenzylamine hydrate (30 g). Through high-performance liquid chromatographic analysis of the thus-obtained p-cyanobenzylamine hydrate, the p-cyanobenzylamine content and the p-xylylenediamine content were found to be 78.5 mass % and 0.4 mass %, respectively. The water content measured through the Karl Fischer method was found to be 21.0 mass %. The yield of p-cyanobenzylamine hydrate, based on the p-cyanobenzylamine contained in the crude p-cyanobenzylamine, was 80%.

PREPARATION EXAMPLE 3

Distillation of p-cyanobenzylamine p-Cyanobenzylamine hydrate (30 g) obtained in Preparation Example 2 was subjected to distillation, thereby yielding 18 g of p-cyanobenzylamine. Through high-performance liquid chromatographic analysis of the thus-obtained p-cyanobenzylamine, the p-cyanobenzylamine content and the p-xylylenediamine content were found to be 99.5 mass % and 0.4 mass %, respectively. The water content measured through the Karl Fischer method was found to be 0.1 mass %.

EXAMPLE 1

In a 200 ml four-neck flask equipped with an agitator, a thermometer, a gas conduit, and a reflux condenser, p-cyanobenzylamine (10.0 g) obtained in Preparation Example 3 was dissolved in ethyl acetate (90.0 g). While the reactor was cooled in a water bath, hydrogen chloride gas was fed into the vapor phase of the reactor while stirring. Immediately after the introduction of hydrogen chloride, heat generation was confirmed, and a white solid was precipitated. After the reaction mixture was cooled to room temperature, the white solid was separated through filtration and dried in a desiccator under vacuum, thereby yielding 12.6 g of p-cyanobenzylamine hydrochloride (yield based on p-cyanobenzylamine: 99%).

Through high-performance liquid chromatographic analysis of the thus-obtained p-cyanobenzylamine hydrochloride, the p-cyanobenzylamine content in the hydrochloride was found to be 77 mass %. In addition, the hydrogen chloride content in p-cyanobenzylamine hydrochloride was found to be 23 mass % through anion chromatographic analysis.

The thus-obtained p-cyanobenzylamine hydrochloride has a bulk density of 0.3 g/ml.

EXAMPLE 2

In a 100 ml three-neck flask equipped with an agitator, a thermometer, and a dropping funnel, p-cyanobenzylamine (6.61 g) obtained in Preparation Example 3 was dissolved in ethyl acetate (60 ml). While the reactor was cooled with an ice bath, sulfuric acid (5.1 g) was added dropwise. Immediately thereafter, heat generation was observed, and a white solid was precipitated. After the reaction mixture was cooled to room temperature, the white solid was separated by filtration, washed with ethyl acetate and dried under normal pressure at 40° C. Thus, 11.4 g of secondary sulfate of p-cyanobenzylamine was obtained (yield: 99%).

Through high performance liquid chromatographic analysis of the obtained secondary sulfate of p-cyanobenzylamine, the p-cyanobenzylamine content in the sulfate was found to be 57 mass %. Further, the sulfate ion content in the sulfate was found to be 43 mass % through anion chromatographic analysis.

EXAMPLE 3

In a 200 ml three-neck flask equipped with an agitator, a thermometer, and a dropping funnel, p-cyanobenzylamine hydrate (32.5 g) obtained in Preparation Example 2 and water (20.2 g) were placed. Concentrated hydrochloric acid (35 mass % aqueous solution of hydrogen chloride, hereinafter the same solution was employed) (20.5 g) was added dropwise to the mixture through the dropping funnel under stirring, thereby forming a white solid. The white solid was separated through filtration and dried in a desiccator under vacuum, thereby yielding 24.5 g of p-cyanobenzylamine hydrochloride (yield based on p-cyanobenzylamine hydrate: 75%).

EXAMPLE 4

By use of a reactor similar to that employed in Example 3, concentrated hydrochloric acid (20.5 g) was added dropwise to a mixture containing p-cyanobenzylamine hydrate (32.8 g) obtained in Preparation Example 2 and the filtrate (39.4 g) obtained through filtration to separate a white solid in Example 3. A white solid was formed, and the solid was separated through filtration and dried in a desiccator under vacuum, thereby yielding 31.0 g of p-cyanobenzylamine hydrochloride.

EXAMPLE 5

By use of a reactor similar to that employed in Example 3, concentrated hydrochloric acid (20.6 g) was added dropwise to a mixture containing p-cyanobenzylamine hydrate (32.5 g) obtained in Preparation Example 2 and the filtrate (52.0 g) obtained through filtration to separate a white solid in Example 4. A white solid was formed, and this solid was separated through filtration and dried in a desiccator under vacuum, thereby yielding 28.0 g of p-cyanobenzylamine hydrochloride.

EXAMPLE 6

By use of a reactor similar to that employed in Example 3, concentrated hydrochloric acid (20.6 g) was added dropwise to a mixture containing p-cyanobenzylamine hydrate (32.6 g) obtained in Preparation Example 2 and the filtrate (68.7 g) obtained through filtration to separate a white solid in Example 5. A white solid was formed, and this solid was separated through filtration and dried in a desiccator under vacuum, thereby yielding 32.1 g of p-cyanobenzylamine hydrochloride.

The total amount of p-cyanobenzylamine hydrate employed throughout Examples 3 to 6 is 130.5 g, and the amount of obtained p-cyanobenzylamine hydrochloride is 115.6 g. Accordingly, the yield of p-cyanobenzylamine hydrochloride based on p-cyanobenzylamine and contained in p-cyanobenzylamine hydrate is 89%.

Through analysis of p-cyanobenzylamine hydrochloride obtained in each of Examples 3 to 6, the p-cyanobenzylamine content was found to be 78 mass %, and the hydrogen chloride content was found to be 22 mass %. No p-xylylenediamine was detected. The water content was found to be 0.1 mass % or less, and the bulk density was calculated to be 0.5 g/ml.

EXAMPLE 7

By use of a reactor similar to that employed in Example 3, concentrated hydrochloric acid (33.4 g) was added dropwise to a mixture containing crude p-cyanobenzylamine (41.3 g) obtained in Preparation Example 1 and water (25.8 g). The resultant mixture was cooled to room temperature, thereby forming white solid. The solid was separated through filtration at room temperature; washed twice with water (10 g×2); and dried under vacuum, thereby yielding 35.2 g of p-cyanobenzylamine hydrochloride (yield as reduced to p-cyanobenzylamine: 70%). Through analysis of the thus-obtained p-cyanobenzylamine hydrochloride, the p-cyanobenzylamine content and the p-xylylenediamine content were found to be 77 mass % and 0.6 mass %, respectively; and the hydrogen chloride content was found to be 22 mass %. The water content was found to be 0.3 mass %, and the bulk density was calculated to be 0.5 g/ml.

COMPARATIVE EXAMPLE p-Cyanobenzylamine hydrochloride was synthesized in accordance with a method described in Japanese International Application Domestic Publication No. 9-509937 as follows.

By use of a reactor similar to that employed in Example 1, N-Boc-p-aminobenzonitrile (5 g) was dissolved in ethyl acetate (100 g). While the reactor was cooled in a water bath, hydrogen chloride gas was fed into the vapor phase of the reactor while stirring, thereby precipitating white solid. After removal of the solvent, the reaction mixture was cooled to room temperature and suspended in diethyl ether. The white solid was separated through filtration and dried in a desiccator under vacuum, thereby yielding 3 g of p-cyanobenzylamine hydrochloride.

Through analysis of the thus-obtained p-cyanobenzylamine hydrochloride, the p-cyanobenzylamine content and the hydrogen chloride content were found to be 77 mass % and 23 mass %, respectively. The bulk density was calculated to be 0.2 g/ml, which was smaller than that attained in the examples of the present invention.

According to the present invention, cyanobenzylamine hydrochloride can be industrially produced through an easy process with good operability. The cyanobenzylamine hydrochloride produced in the present invention, having a bulk density higher than that of conventionally produced hydrochloride, is beneficial from the viewpoints of distribution and handling.

We claim:

1. A process for producing a salt of a cyanobenzylamine comprising reacting a cyanobenzylamine represented by the following formula with an acid using water as a solvent:

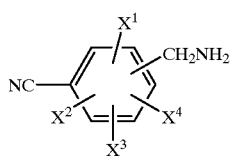

wherein $X^1$, $X^2$, $X^3$, and $X^4$ each independently represent a hydrogen atom, an alkyl group having 1 to 3 carbon atoms or a halogen atom, and the —CH$_2$NH$_2$ group may be at any position of ortho, meta or para to the —CN group.

2. The process as claimed in claim 1, wherein the cyanobenzylamine is hydrate thereof.

3. The process as claimed in claim 1, wherein the acid is selected from the group consisting of hydrogen chloride, sulfuric acid, acetic acid, trifluoroacetic acid and propionic acid.

4. The process as claimed in claim 3, wherein the acid is used in the form of an aqueous solution.

5. The process as claimed in claim 3, wherein the acid is hydrogen chloride.

6. The process as claimed in claim 3, wherein a cyanobenzylamine containing an impurity soluble in an aqueous solution of the acid is used.

7. The process as claimed in claim 6, wherein the impurity soluble in an aqueous solution of the acid is xylylenediamine, and the salt of a cyanobenzylamine is hydrochloride of the cyanobenzylamine.

8. The process as claimed in claim 1, wherein the cyanobenzylamine is used after distillation.

9. The process of claim 1, wherein the cyanobenzylamine is p-cyanobenzylamine.

10. A salt of cyclobenzylamine, wherein the cyanobenzylamine is represented by the following formula

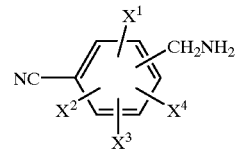

wherein $X^1$, $X^2$, $X^3$, and $X^4$ each independently represent a hydrogen atom, an alkyl group having 1 to 3 carbon atoms or a halogen atom, and the —CH$_2$NH$_2$ group may be at any position of ortho, meta or para to the —CN group, having a bulk density of 0.4 g/ml or more.

11. The salt as claimed in claim 10, which is a salt of p-cyanobenzylamine.

12. The salt as claimed in claim 11, which is p-cyanobenzylamine hydrochloride.

13. The process according to claim 1, wherein a cyanobenzylamine having a bulk density of 0.4 g/ml or more is produced.

* * * * *